United States Patent [19]

Pinder

[11] 4,091,803
[45] May 30, 1978

[54] TRANSDUCERS

[75] Inventor: Russell Stuart Pinder, Newcastle-upon-Tyne, England

[73] Assignee: Thomas Orr, Southampton, England

[21] Appl. No.: 656,842

[22] Filed: Feb. 9, 1976

[30] Foreign Application Priority Data

Feb. 17, 1975 United Kingdom ............... 6668/75

[51] Int. Cl.$^2$ .............................................. A61B 5/02
[52] U.S. Cl. ........................... 128/2.05 P; 128/2.05 T; 338/15; 357/30
[58] Field of Search ............... 128/2.05 P, 2.05 T, 128/2.05 E, 2.05 R, 2.05 V, 2 L; 338/15; 357/30; 356/39–41

[56] References Cited

U.S. PATENT DOCUMENTS

| 2,820,841 | 1/1958 | Carlson et al. | 357/30 X |
| 3,139,086 | 6/1964 | Botsch et al. | 128/2.05 P |
| 3,228,391 | 1/1966 | Fitter | 128/2.05 T |
| 3,238,062 | 3/1966 | Sunners et al. | 357/30 X |
| 3,289,024 | 11/1966 | De Haan et al. | 357/30 X |
| 3,602,213 | 8/1971 | Howell | 128/2.05 P X |
| 3,704,706 | 12/1972 | Herczfeld et al. | 128/2.05 P X |
| 3,769,974 | 11/1973 | Smart et al. | 128/2.05 P |
| 3,807,388 | 4/1974 | Orr et al. | 128/2.05 T X |
| 3,810,460 | 5/1974 | Van Nie | 128/2.05 E |

FOREIGN PATENT DOCUMENTS

| 2,136,823 | 2/1973 | Germany | 128/2.05 T |
| 2,245,214 | 3/1973 | Germany | 357/30 |

Primary Examiner—Robert W. Michell
Assistant Examiner—Lee S. Cohen
Attorney, Agent, or Firm—Mason, Fenwick & Lawrence

[57] ABSTRACT

A transducer for optically detecting a cyclic phenomenon of variable frequency and supplying an electric signal corresponding to the frequency, comprises a light source for illuminating the site of the phenomenon and a detector for detecting variations in the level of light reflected from the site of the phenomenon and providing the required electric signal, the detector being a semiconductor opto-electronic cell and the light source being positioned within the detector.

3 Claims, 3 Drawing Figures

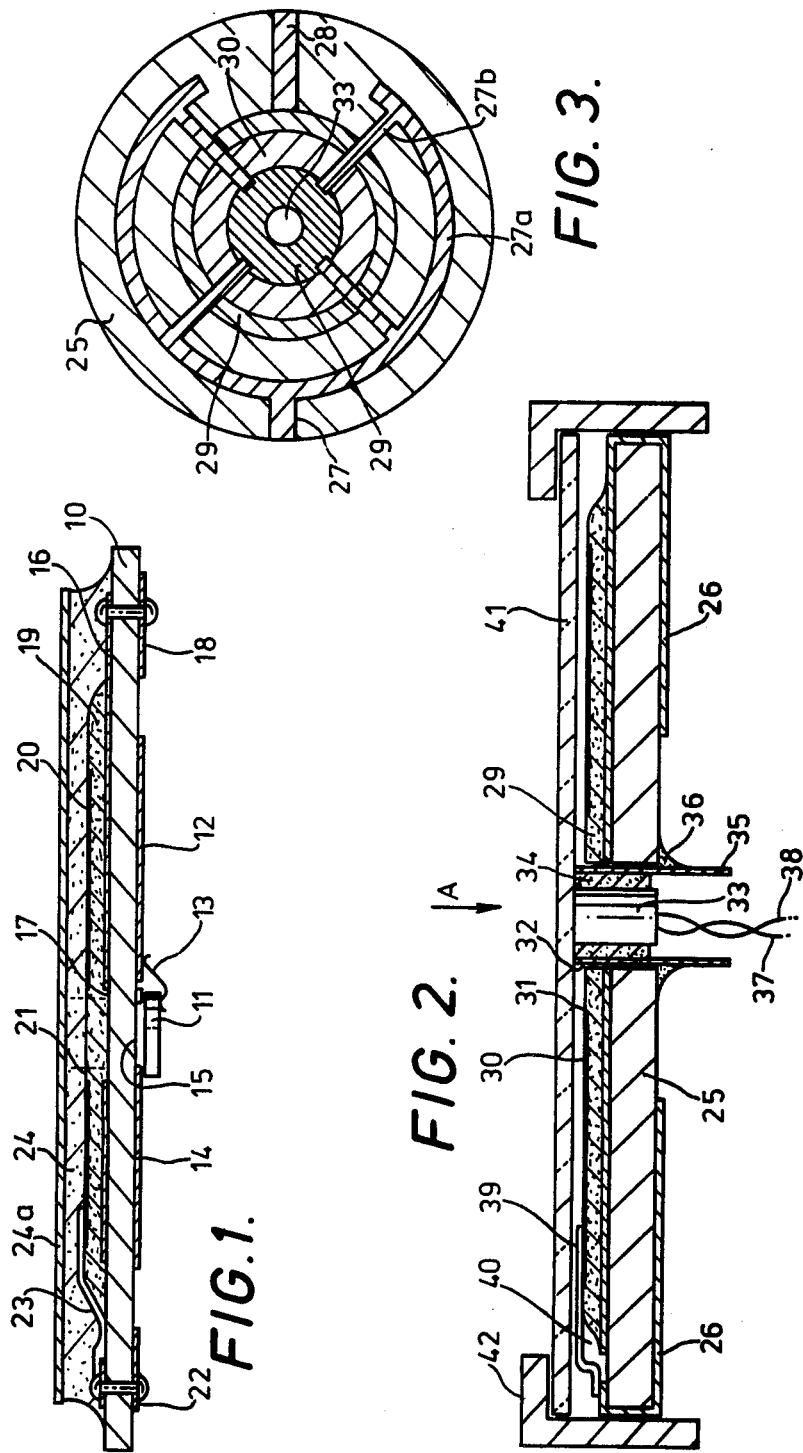

TRANSDUCERS

RELATED PATENT

Transducers according to the present invention may be used in heartbeat rate monitors as disclosed and claimed in U.S. Pat. No. 3,807,388 issued Apr. 30 1974 and having a common assignee with the present application.

BACKGROUND OF THE INVENTION

In the above-mentioned patent there is disclosed and claimed a heartbeat rate monitor and personal pulse indicator wherein a watch casing includes timing means, transducer means for the detection of heartbeats, a comparator means wherein there is derived from the timing signal and transducer a signal representing the heartbeat rate per unit time and display means representing the time of day and the heartbeat rate.

SUMMARY OF THE INVENTION

One object of the present invention is to provide a transducer suitable for use in detecting heartbeat rate.

Another object of the present invention is to provide a transducer for detecting a cyclic variation, and comprising a light emitting diode and a semiconductor opto-electronic detector.

According to the present invention there is provided a transducer for optically detecting a cyclic phenomenon of variable frequency and supplying an electric signal corresponding to said frequency, the transducer comprising a light source for illuminating the site of the phenomenon, and a detector for detecting variations in the level of light reflected from said site and supplying the required said electric signal, the detector being a semiconductor opto-electronic cell and the light source being positioned within said detector.

According to the present invention there is also provided a transducer to detect heartbeats and provide an electric signal, the frequency of which corresponds to heartbeat rate, which transducer comprises a light source to transilluminate skin tissue and detection means for detecting variations in the reflected light level from the skin tissue so as to produce an electric signal responsive to changes in arterial blood flow.

It should be understood that the term "arterial blood flow" does not necessitate the positioning of the transducer over an artery; it will function in regions of capillaries.

Preferably the light source is a light emitting diode and the detector is an opto-electronic cell which detects variations in the reflected light level.

The opto-electronic detector is preferably a photoconductive cell, for example cadmium sulfide or cadmium selenide or a photo-voltaic diode, for example silicon, selenium or cadmium sulfide/coprous sulfide.

The transducer may preferably comprise a thin photo-conductive cell or photo-voltaic diode with a centrally positioned light emitting diode, which may be of gallium phosphide, gallium arsenide phosphide, or gallium arsenide.

The transducer is preferably so arranged as to minimize the impingement of stray light from the light source to ensure that the major proportion of light received by the detector is that reflected by transillumination of the skin tissue to which the transducer is applied.

The transducer is preferably positioned on the rear surface of a watch and may be provided with a flexible seal around the perimeter of the transducer to shield the transducer from extraneous light sources whilst maintaining good contact with the surface of the skin to which it is applied.

BRIEF DESCRIPTION OF THE DRAWINGS

The invention will now be described by way of example with reference to the accompanying drawings, in which:

FIGS. 1 and 2 are cross-section elevations of first and second embodiments respectively, and FIG. 3 is a plan view of the second embodiment.

DESCRIPTION OF THE PREFERRED EMBODIMENTS

The first embodiment will now be described with reference to FIG. 1, which is a cross-sectional elevation of a transducer comprising a transparent substrate 10 on the underside of which is mounted a light emitting diode 11 with connections for energisation comprising a metal base contact 12 and lead 13, and a metal top contact 14. The contact 14 has a circular aperture 15 through which light from the LED 11 is emitted. On the upper face of the substrate 10 there is deposited an annular base metallization contact 16 having a circular aperture 17, the contact 16 being connected to an output circuit (not shown), by means of a through hole terminal 18. A photo-voltaic PN junction is formed by depositing a layer 19 of cadmium sulfide (CdS) over the contact 16 and superimposing an annular layer 20 of coprous sulfide ($Cu_2S$) having a circular aperture 21. The layer 20 is connected to a through hole terminal 22 by a contact 23, and finally the upper portion of the assembly is encapsulated in a transparent resin layer 24, at least the surface layer 24a of which should be compatible with human skin and neither cause nor suffer any adverse reaction after prolonged skin contact. The encapsulation medium may be shaped to achieve optimum performance, for example by having a concave outer surface and relying upon the perimeter of a watch case on which the transducer is mounted to provide an adequate light seal. Alternatively, a flexible seal may be provided.

The apertures 15, 17 and 21 are so dimensioned and positioned to ensure that the light emitted from LED 11 does not impinge on the associated contacts and layers.

The transducer may be used in a heartbeat rate detector as described in the above-mentioned patent, and make use of the electronic circuitry shown and described with reference to FIGS. 5, 6 and 7 of that patent.

Although the transducer can be operated with a dc input, it is preferable for operation to be effected by energization of the LED 11 with a pulse input, or at least a cyclic input, having a frequency much higher than the normal heartbeat rate. Thus the frequency of the input may be 1000 Hz, and is applied through contacts 12 and 14. The light is then emitted in the form of pulses from the LED 11, and passes through apertures 15, 17 and 21, so as to transilluminate the adjacent skin tissue. The light is reflected back from the skin tissue and impinges upon the active surface of the transducer, that is the $Cu_2S$ layer 20, to produce an output signal to contacts 18 and 22, the modulation frequency of the output signal corresponding to the heartbeat rate.

The second embodiment will now be described with reference to FIGS. 2 and 3, FIG. 2 being a cross-sectional elevation and FIG. 3 being a plan in the direction of arrow A in FIG. 2, of a transducer comprising a glass substrate 25 on to which there is laminated an insulating plastics film 26 which serves to insulate discrete metallised contact regions 27, 27a, 27b and 28, from the substrate 25 and provide for electrical connection to the transducer.

A photo-voltaic PN junction is formed by depositing a CdS layer 29 on the upper region of a metallised portion of the film 26 and further depositing an annular $Cu_2S$ layer 30 having a central aperture 31.

A through aperture 32 is formed in the substrate 25, CdS layer 29 and film 26, and a light source package comprising an LED 33 fixed with epoxy resin 34 inside an open-ended stainless steel tube 35 is positioned within the aperture 32 and fixed by epoxy resin 36. Leads 37 and 38 are provided for energisation of the LED 33.

The $Cu_2S$ layer 30 is electrically connected to a contact 39 by the region 27, "C" shaped region 27a and radial regions 27b. Electrical connection to the CdS layer 29 is by way of region 28. Regions 27 and 28 are both formed to pass to the underside of the substrate 25 for provision of electrical output contacts.

The complete assembly thus far described is surmounted by glass encapsulation 41 and contained within a flanged annular stainless steel bezel ring 42 which is used for mounting the transducer in, for example, the back of a wrist watch. The inside surface of the bezel is provided with an insulating layer to prevent electrical short-circuiting of the regions 27, 27a, 27b and 28. Operation of the transducer is generally as described with reference to FIG. 1, except that the energising pulses are fed to LED 33 by leads 37 and 38. The light is emitted in the form of pulses from the LED 33 and the opaque walls of the tube 35 ensure that impingement of stray light on the transducer elements 25, 26, 29 and 30 is minimised. Transillumination of the skin tissue, to which the transducer is applied, occurs and the light is reflected back from the skin tissue to impinge on the active surface of the transducer, that is the $Cu_2S$ film 30 to produce an output signal which is derived from regions 27 and 28.

The output may be fed to circuits as described in the above-mentioned patent, or similar circuits.

Human skin is a reasonably good transmitter of visible and near infra-red light and, within the outer layers at least, no changes in transmission or absorption are observed over the short time periods under consideration. However, the inner layers of skin tissue are supplied with blood for their correct functioning, and it is the interaction of this blood with incident light that produces changes in the reflected light level. Skin tissue is supplied with arterial blood from the heart via a complex network of arterioles and capillaries. Arterial blood flows in pulses which decrease in intensity along the arterial circuit, the major drop in pulse height occuring before the capillary bed flow stage. Thus the venous blood return circuit can be ignored.

The main arteries are usually deep seated, but the arterioles and capillaries are much closer to the skin surface and are arranged in complex parallel coupled circuits between the arteries and veins.

While the arterioles and capillaries are quite elastic to the blood pulse, it is thought to be certain properties of blood, rather than the movement of vascular walls under the skin surface, that give rise to the reflectivity changes. There are two mechanisms which may account for these changes, both are complex and interrelated, and they relate to:

(a) the volume of a blood pulse within the skin tissue, and (b) oxygen content of the blood.

Considering these two absorption phenomena together, and assuming that light absorption due to the volume of blood within the arterial pulse wave is the dominant effect, it appears that the use of light within the wavelength range 500 to 600 nm would give rise to the maximum light absorption during the blood pulse. However, there obviously has to be sufficient reflected light from the blood content of the skin tissue to activate the transducer, and operation of the light source within the range 600 to 650 nm will produce a lower absolute value of light absorption level, and therefore a higher intensity of reflected light.

A signal change is also produced due to the change in oxygen content of the blood during the arterial pulse, and this will tend to reduce slightly the absorption maximum to be expected during the peak of the arterial pulse, and therefore the amplitude of the signal.

The outer surface of the human skin is known to exhibit a spectrally sensitive transmission factor, but over the range under consideration there are no major changes in transmission levels to warrant further attention.

This invention is not restricted to the form of transducer described by way of example, nor to use with the electronic circuitry described in the above-mentioned patent; alternative configurations and circuitry may be employed. Thus in general the signal derived from the transducer will be used to activate a display, which may be a liquid crystal display, indicating the heartbeat rate, although in some cases the signal may be used to activate a remote alarm if the heartbeat rate moves outside a predetermined range, or a remote indicator. Such forms are particularly useful for divers or pilots or those working in a hazardous environment. In all cases the heartbeat rate can be recorded if necessary.

A transducer associated with a remote alarm may form the basis of a baby monitor for use for example in incubators in which prematurely born babies are placed. It has been found that a good signal can be obtained by positioning the transducer on a baby's forehead.

Again, although the transducer and the associated display means may be housed in a watch casing, for example a wrist watch casing, it is not essential for the watch casing also to provide a time display. Such forms of the invention provide very convenient and readily portable heartbeat rate monitors, which can incidentally be used to determine very rapidly whether an injured person is alive or not, merely by placing the monitor on an exposed part of the person's skin.

If a time display is also provided, the heartbeat rate and the time display may both be displayed continuously and simultaneously or, to save electric power, one or both of the displays may be provided only when selected by the user.

Although the embodiments have been described in relation to heartbeat rate measurement, the transducers described are suitable for optical detection of a wide range of cyclic phenomenon of variable frequency from liquid flow to pattern recognition.

I claim:

1. A transducer for detecting heartbeats and supplying an output signal in dependence thereon with a frequency component of the output signal corresponding to a heartbeat rate to be detected, said transducer comprising a light emitting diode and a planar opto-electronic detector which is a photo-conductive cell encircling said light emitting diode and which comprises an electrically insulating substrate, an insulating film on said substrate, a photo-voltaic PN junction on the surface of said insulating film comprising a layer of cadmium sulfide and an annular disc of cuprous sulfide on the surface of said layer of cadmium sulfide to provide a light sensitive surface layer, first and second output terminals, conductor means connecting each of said output terminals to a respective one of said layers, the transducer adapted to be mounted on a watch case component means positionable adjacent the skin of a user with the light emitting diode facing the skin of the user to emit light thereagainst being energizable by a periodic signal from a source contained in said watch case component means, the light emitting diode being positioned when in use to emit light toward a surface of skin tissue of a user to transilluminate said surface of skin tissue to cause the surface of skin tissue to emit light and the opto-electronic detector encircling said light emitting diode so as to be positioned in close proximity to said surface of skin tissue so that the majority of light originating from said light emitting diode emitted from said surface of skin tissue is directed into said opto-electronic detector which detects variations in the reflected light level from said surface of skin tissue and provides said output signal to said first and second output terminals in response to changes in arterial blood flow.

2. A transducer positionable adjacent the skin of a user to detect heartbeats and provide an electric signal the frequency of which corresponds to heartbeat rate, the transducer comprising a light source positioned adjacent the skin of the user to transilluminate an area of said skin tissue and detector means for detecting variation in the reflected light level from the skin tissue so as to produce an electric signal responsive to changes in arterial blood flow, said light source comprising a light emitting diode having power input leads connectible to a source of periodic input signals accommodated in a watch housing, the light emitting diode being positioned centrally within said detector means, the detector means comprising of an opto-electronic cell, said cell including an electrically insulating substrate, an insulating film on said insulating substrate, a photo-voltaic PN junction formed on said insulating film, said PN junction including a layer of cadmium sulfide on said insulating film and an annular disc of cuprous sulfide on the surface of said layer of cadmium sulfide to provide a light sensitive surface layer, first and second output terminals, means defining electrically conductive paths on said insulating film on said substrate for connecting each of said terminals to a respective one of said layers.

3. A transducer according to claim 2, wherein said light emitting diode emits light having a wavelength in the range of 600 to 650 nm.

* * * * *